United States Patent
Liu et al.

(10) Patent No.: US 10,670,514 B2
(45) Date of Patent: Jun. 2, 2020

(54) SENSOR FOR PARTICLE DETECTION IN A FLUID

(71) Applicant: Water Optics Technology PTE. LTD, Singapore (SG)

(72) Inventors: Ai Qun Liu, Singapore (SG); Lei Lei, Singapore (SG); Wei Huang, Singapore (SG); Shahnawaz Pukkeyil Shamsuddin, Singapore (SG)

(73) Assignee: Water Optics Technology Pte. Ltd., Singapore (SG)

( * ) Notice: Subject to any disclaimer, the term of this patent is extended or adjusted under 35 U.S.C. 154(b) by 328 days.

(21) Appl. No.: 15/516,369

(22) PCT Filed: Oct. 1, 2014

(86) PCT No.: PCT/SG2014/000462
§ 371 (c)(1),
(2) Date: Mar. 31, 2017

(87) PCT Pub. No.: WO2016/053181
PCT Pub. Date: Apr. 7, 2016

(65) Prior Publication Data
US 2017/0248513 A1 Aug. 31, 2017

(51) Int. Cl.
*G01N 15/14* (2006.01)
*C12Q 1/00* (2006.01)
(Continued)

(52) U.S. Cl.
CPC ............ *G01N 15/1484* (2013.01); *B01L 1/00* (2013.01); *B01L 3/502761* (2013.01);
(Continued)

(58) Field of Classification Search
CPC ........... G01N 15/1484; G01N 33/1826; G01N 29/022; G01N 15/1404; G01N 15/1459;
(Continued)

(56) References Cited

U.S. PATENT DOCUMENTS

| 5,870,186 A * | 2/1999 | Mogan | G01N 15/02 |
| | | | 250/573 |
| 2003/0182068 A1* | 9/2003 | Battersby | B01J 19/0046 |
| | | | 702/22 |

(Continued)

FOREIGN PATENT DOCUMENTS

| CN | 102762990 B | 10/2014 |
| JP | 5013410 B2 | 8/2012 |

OTHER PUBLICATIONS

Vang, Oluva Karin, "ATP measurements for monitoring microbial drinking water quality." DTU Environment, 2013.

*Primary Examiner* — Randy W Gibson
*Assistant Examiner* — Gedeon M Kidanu
(74) *Attorney, Agent, or Firm* — Muir Patent Law, PLLC (57) ABSTRACT

A sensor is provided for detecting and characterizing particles in a fluid. The sensor has a microfluidic channel for receiving the fluid sample, an acoustic transducer module configured to generate a standing wave for concentrating the particles in a region of the microfluidic channel; an optical detection module configured to detect optical signals scattered by the particles upon illuminating the region of the fluid sample with a light source; and a data processing module configured to characterize the particles of the fluid sample based on the optical signals using a classifier.

2 Claims, 7 Drawing Sheets

(51) Int. Cl.
*B01L 3/00* (2006.01)
*B01L 1/00* (2006.01)
*G01N 33/18* (2006.01)
*G01N 37/00* (2006.01)
*G01N 29/02* (2006.01)
*G01N 15/10* (2006.01)
*G01N 35/08* (2006.01)

(52) U.S. Cl.
CPC ........... *C12Q 1/00* (2013.01); *G01N 15/1404* (2013.01); *G01N 15/1459* (2013.01); *G01N 29/022* (2013.01); *G01N 33/1826* (2013.01); *G01N 37/00* (2013.01); *B01L 2400/0436* (2013.01); *G01N 35/08* (2013.01); *G01N 2015/1006* (2013.01); *G01N 2015/1409* (2013.01); *G01N 2015/1415* (2013.01); *G01N 2015/1497* (2013.01)

(58) Field of Classification Search
CPC ................... G01N 37/00; G01N 35/08; G01N 2015/1409; G01N 2015/1006; G01N 2015/1415; G01N 2015/1497; B01L 3/502761; B01L 1/00; B01L 2400/0436
See application file for complete search history.

(56) References Cited

U.S. PATENT DOCUMENTS

| | | | |
|---|---|---|---|
| 2006/0139638 A1* | 6/2006 | Muller | G01N 15/12 356/342 |
| 2008/0003678 A1* | 1/2008 | Hattori | B01L 3/502753 435/383 |
| 2008/0213821 A1* | 9/2008 | Liu | B01L 3/502761 435/39 |
| 2008/0255705 A1* | 10/2008 | Degeal | B07C 5/342 700/273 |
| 2009/0178716 A1* | 7/2009 | Kaduchak | G01N 15/1404 137/13 |
| 2011/0134426 A1* | 6/2011 | Kaduchak | G01N 15/1404 356/337 |
| 2011/0169837 A1* | 7/2011 | Takata | G01N 15/14 345/440.2 |
| 2014/0048458 A1* | 2/2014 | Ito | B07C 5/3416 209/577 |
| 2015/0268244 A1* | 9/2015 | Cho | G01N 33/57492 435/7.23 |
| 2015/0347817 A1* | 12/2015 | Valvik | G06T 5/50 382/133 |

* cited by examiner

SENSOR FOR PARTICLE DETECTION IN A FLUID

FIELD OF INVENTION

The invention relates to a sensor for detecting a particle in a fluid, and more particularly to an optofluidic sensor for detecting and identifying pathogenic microorganisms in a fluid, such as water.

BACKGROUND

Detection and control of the pathogenic microorganisms in water, especially in portable water, is a big concern as these health-affected contaminants in potable water may cause a fatal outbreak especially in a densely-populated city [1].

There are existing conventional laboratory methods for detecting certain known types of pathogenic microorganisms. These conventional microbiological laboratory methods have some intrinsic limits such as long processing time, and high cost. Furthermore, they are laborious with a need for skilled technicians and ineffective for onfield monitoring.

Moreover, there is a limit to the types of microorganisms that conventional laboratory methods are able to detect. These methods typically require the following steps: sampling, culturing, isolation, staining and quantification by microscopic method. However, some pathogens, such as *Cryptosporidium parvum* (*C. parvum*) and *Giardia lamblia* (*G. lamblia*), are impossible to culture. This is an important constraint for these conventional methods because quite a few waterborne outbreaks are in fact caused by emerging pathogenic microorganisms or even modified organisms—which conventional laboratory methods are not able to detect.

Currently, the most widely accepted protocol for their analysis is US-EPA 1623 method [3]. First, the water is collected and shipped to a laboratory in a volume ranging from 10 to 1000 L, depending on the expected organism level. The water sample is then sent to a filter and is concentrated into a smaller volume. Pathogens can be then further concentrated through centrifugation and screened out by the use of an immune-magnetic separation method [4]. The final concentrated organisms are then stained and manually counted by a fluorescence microscope. The time required by this method or other conventional microbiological methods to yield results is normally from 24 to 72 hours, which is not practical to provide an event warning.

In recent years, some other methods like the polymerase chain reaction (PCR) and flow cytometry are also used for the water pathogens detection. Note that flow cytometry requires fluorescent labeling for particle identification. However, many microorganisms in water do not have the specific stain chemicals for labeling. Although flow cytometry may detect a scattering intensity of a particle, it is used for counting particle count instead of identifying particles (such as bacteria) since the scattering intensity is mostly based on the particle size—which would not be reliable for particle identification. Therefore, it is difficult to use the flow cytometry for pathogen detection in water. Moreover, these methods are still laboratory based, labor-intensive, and high cost due to the consumption of the bio-reagents.

Therefore, there is a need for an improved method and device for detecting and identifying pathogens in water to allow real-time and on-site monitoring of waterborne pathogens. It is also desired to develop a modern water risk management system and method with an automated working process with low-cost, fast, reliable detection of pathogenic microorganisms in water.

SUMMARY OF INVENTION

In general terms, the invention proposes using an acoustic wave to provide pressure differential across different positions of a fluid in a microfluidic channel thereby concentrating ("focusing") particles in a fluid into at least one region of the channel (typically a centre region) for particle characterization. The invention also proposes using a forward scattering pattern of a particle in a fluid to characterize or identify the species of the microorganism particle.

Specifically, in an aspect of the invention, there is provided a sensor for characterizing particles in a fluid sample, comprising:

a microfluidic channel for receiving the fluid sample, an acoustic transducer module configured to generate a standing wave for concentrating the particles into at least one region of the microfluidic channel;

an optical detection module configured to detect optical signals scattered by the particles upon illuminating the at least one region of the fluid sample with a laser source; and a data processing module configured to characterize the particles of the fluid sample based on the optical signals using a classifier.

By acoustically concentrating the particles in the detection area, optical signals can be obtained which characterize the particles. The data processing module may classify the particles into respective pre-defined categories in real time by the classifier.

Advantageously, the sensor does not require the microorganisms to be cultured before they get detected by the sensor. Similarly, no labeling of any kind (such as fluorescent labeling in flow cytometry) is required.

Typically, the standing wave generates a pressure differential across different positions in the microfluidic channel thereby altering a path along which the particles flow through the microfluidic channel at the respective positions. Typically, the acoustic transducer module has an ultrasound transducer.

Advantageously, the particles are controlled to flow through a pre-defined area along the microfluidic channel for their optical signals to be detected. This concentration can simply be achieved by creating a standing wave in the microfluidic channel. In one embodiment, the microfluidic channel has two major opposing walls separated by a distance (d), the acoustic transducer module is configured to generate a standing wave of a wavelength ($\lambda$) of 2d.

Preferably, the acoustic transducer module is configured to generate a first standing wave oscillating in a direction orthogonal to that of a second standing wave in the microfluidic channel; said first and second directions being orthogonal also to a direction of the microfluidic channel along which the fluid is configured to flow. The first standing wave preferably produces a pressures node which coincides with that produced by the second standing wave.

Preferably, the pressure differential causes the particles to converge along a pre-defined path in the microfluidic channel.

This is advantageous since the pressure differential allows the particles to be moved along a pre-defined path to sequentially pass through the same detection area (which could be made very small) to minimize variations and random errors (e.g. caused by differences in the particle-detector distances, etc.) in the optical signals detection for different particles.

In one embodiment, the pre-defined path is a center path defined by the geometrical centers of a plurality of cross-sections of the microfluidic channel. The plurality of cross-sections are orthogonal to a direction of the microfluidic channel along which the fluid is configured to flow. In this way, the particles are concentrated into the center of the microfluidic channel as the fluid flows.

In one embodiment, the optical detection module has a first sensor module configured to detect a forward scattering pattern of the microorganism particle. Optionally, a second sensor module is provided to detect a side-scattering signal such as intensity of the particle. Using a combination of the forward scattering pattern and the side scattering signal provides more information as to the morphologies and biophysical properties of the particles which enables a more accurate characterization or identification of the particle.

The first sensor module may be configured to be activated by the second sensor module and/or the side-scattering signal. Therefore, continuous monitoring and capturing of the forward scattering pattern of the particles are not required which makes the system more efficient since the computational load is reduced.

The optical detection module may be removably attached to the sensor or integral to the sensor.

The microfluidic channel may have more than one outlets. For example, a main outlet can be provided for discharging the particles as the fluid flows out of the channel. One or more side outlets may be provided to discharging any redundant fluid sample only. This may be achieved by for example, concentrating the particles along a path leading to the main outlet thereby directing the particles away from the side outlets. In this way, the requirements for pre-concentration of sample may be reduced.

The particles may be microorganism particles. In one embodiment, the classifier may be configured to identify the species of the respective microorganism particles. Optionally, the classifier is configured to further identify if the microorganism particles are viable. This allows the pathogenic risk of the water to be more closely and accurately identified, which can be hard by conventional methods.

In a further embodiment, the particles are blood cells. The blood cells may be characterized as the respective types of cells such as red blood cell or white blood cell.

In one embodiment, the classifier characterizes the particles based on a comparison between the optical signals and a plurality of reference signals representing signal profiles of known microorganism particles. Optionally, the plurality of reference signals are obtained based on measured scattering signals of known particles. By utilizing knowledge of optical signatures of known particles, the characterization of particles by their optical signals can be achieved.

In one embodiment, the classifier employs a machine learning algorithm to extract features of the optical signals of the particles and assign the respective particles into respective categories based on the features. In this way, the classifier can be trained to extract the key features of the optical signals such that the optimal characterization or classification accuracy could be achieved.

In another aspect of the invention, there is provided a method of characterizing particles comprising:
  receiving a fluid sample containing the particles into a microfluidic channel;
  generating a standing wave to concentrate the particles into at least one region in the microfluidic channel;
  detecting optical signals scattered by the particles upon at least one region of the fluid sample being illuminated with a light source; and
  characterizing the particles based on the optical signals using a classifier.

The particles may be microorganism particles.

In a further aspect of the invention, there is provided a method of classifying particles in a fluid sample.

The method comprises illuminating the particle with a light source;
  detecting optical signals scattered by the particle; wherein the optical signals comprises a forward scattering pattern; and
  characterizing the particle into one of a plurality of categories based on the forward scattering pattern.

In one embodiment, the method comprises detecting a side scattering signal such as a side scattering intensity by the particle. Optionally, the method comprises activating a mechanism for detecting the forward scattering pattern upon a detection of the side scattering signal.

In one embodiment, the particles are microorganism particles. The method may further comprise identifying the species of the microorganism particles and optionally identifies if the microorganism particles are viable.

In another embodiment, the characterizing step includes comparing the optical signals with a plurality of reference signals representing signal profiles of known particles. The plurality of reference signals may be obtained based on measured scattering signals of known particles. The reference signals are typically derived from forward scattering patterns of known particles.

In another embodiment, the classifier employs a machine learning algorithm to extract features of the optical signals of the particles and assign the respective particles into respective categories based on the features.

In yet a further aspect of the invention, there is provided a method of managing risk of pathogens in a fluid comprising:
  (a) receiving optical signals scattered by a microorganism particle in the fluid; said optical signals comprising a forward scattering pattern;
  (b) characterizing the microorganism particle into one of a plurality of categories based on the forward scattering pattern using a classifier; (c) updating a record data representing the number of microorganism particles of the plurality of categories;
  (d) determining a risk level based on the record data;
  (e) determining, if a termination criterion is met based on a comparison of the risk level to a reference risk level and, if not, returning to step (a) until a termination criterion is met; and
  (f) upon the termination criterion being met, producing a warning signal indicating an elevated risk of pathogens in the fluid.

The fluid may be water.

In one embodiment, the method comprises receiving a side scattering signal such as a side scattering intensity by the microorganism particle. In one embodiment, the method further comprises comparing the side scattering signal intensity with an initiation threshold before the forward scattering pattern is captured.

In another embodiment, step (b) further comprises identifying the species of the microorganism particles. Optionally, the method further comprises identifying if the microorganism is viable.

In one embodiment, the record data comprises a respective count of microorganism particles in the respective categories.

In one embodiment, the method further comprises treating the water based on the risk level.

In yet a further aspect of the invention, there is provided a fluid risk management system comprising a computer processor and a data storage device which stores instructions operative by the processor to cause the processor to perform the method above.

The term forward scattering "pattern" means forward scattering signals collected at a range of angles (such as −45° to +45° or −60° to +60°) with respect to the light beam, as compared to a forward scattering amplitude typically collected at a single (or else very narrow range of) angle. Such a forward scattering pattern is typically formed as a two-dimensional image representing the distribution of forwardly scattered photons.

The term "characterize" a particle or particles means associating one or more attributes with the particle(s) which allows an identity of one particle to be distinguished from another (i.e. to classify particles into a plurality of categories). For example, "characterizing" in relation to particles may include identify if the particle is silt, sand or bacteria. For another example, "characterizing" in relation to microorganisms may include identifying the species and/or sub-species of the microorganism. It may further include identifying whether the microorganism is viable or not. For a further example, "characterizing" in relation to blood cells may include identifying the type (e.g. red or white blood cell) of blood cell or a diseased state of a blood cell (e.g. sickle cell or normal red blood cell). Preferably the associated attributes of the particle(s) comprise at least one attribute other than the size of the particles.

By "about" in relation to a given numerical value such as for dimensions, frequencies, wavelengths, and power, it is meant to include numerical values within 10% of the specified value.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

FIG. 3(a) and FIG. 3(b) are photographs captured by a CCD camera mounted on a fluorescence microscope showing the suspension of 5-μm fluorescent polystyrene particles flowing through the microfluidic channel when an acoustic transducer module is (a) off and (b) on.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural changes may be made without departing from the scope of the invention. The various embodiments are not necessarily mutually exclusive, as some embodiments can be combined with one or more other embodiments to form new embodiments.

Figure 1:
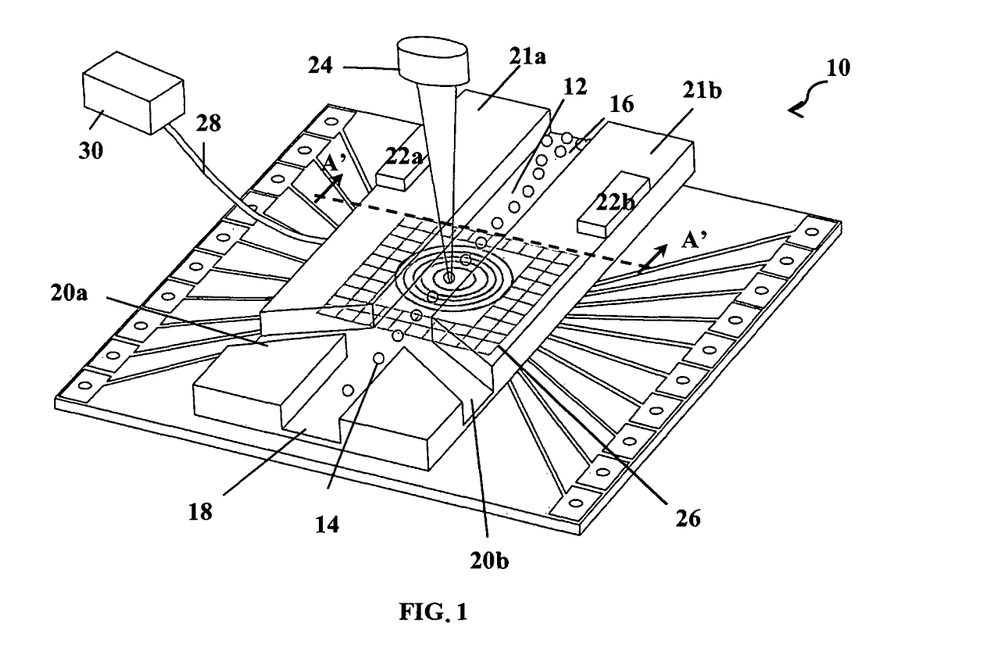
FIG. 1 is a schematic illustration of a sensor according to an embodiment of the invention.

FIG. 1 is a schematic diagram of a sensor for detecting microorganism particles in a fluid. In this particular example, the sensor 10 is adapted to detect waterborne pathogens in water. The optofluidic sensor 10 has a microfluidic channel 12 configured to allow a water sample containing microorganism particles 14 to flow through. The microfluidic channel has an inlet 16 for receiving the water sample and a main outlet 18 for discharging the water sample. The microfluidic channel 12 further has two ancillary outlets 20a, 20b disposed symmetrically along the microfluidic channel 12 for discharging redundant water.

The optofluidic sensor 10 includes two ultrasound transducers 22a, 22b located proximate to the microfluidic channel 12 for generating an acoustic force for concentrating the particles 14 in the microfluidic channel 12. In a specific example, the two ultrasound transducers 22a, 22b are attached to two respective side walls 21a, 21b of the microfluidic channel 12, and each of them is configured to generate an ultrasound standing wave oscillating in a direction orthogonal to the one generated by the other. In this example, the standing waves are oscillating in the lateral direction 38a and vertical direction 38b, both of which are orthogonal to the direction along which the fluid flows in the microfluidic channel 12.

Figure 2:
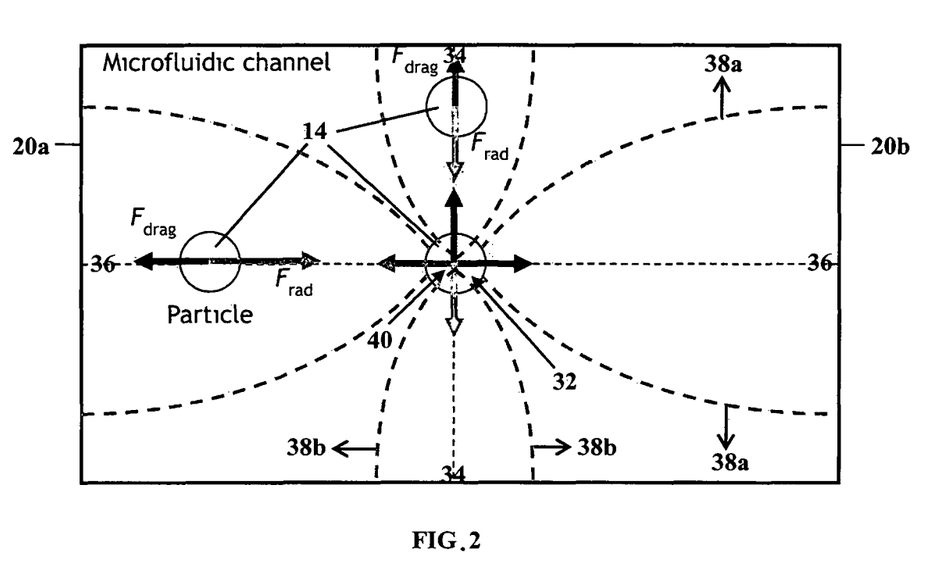
FIG. 2 shows the forces acted on the particles when an ultrasound standing waves are produced in the microfluidic channel viewing from a cross-section of the microfluidic channel along A'-A'.

In one embodiment, the width of the microfluidic channel 12 is set to be half of the wavelength ($\lambda/2$) of the ultrasonic wave generated by the transducers. In use, this creates a standing wave between the two side walls 21a, 21b of the microfluidic channel 12. Suspending particles 14 will be pushed to pressure nodes formed by the standing wave. In one example, a pressure node 32 is created at the mid-point between the two side walls of the microfluidic channel 12, while two anti-nodes 34, 36 are created at both sides of the microfluidic channel 12 adjacent to the side walls, as shown in FIG. 2.

When an ultrasound standing wave is established in the microfluidic channel 12 filled with suspending particles 14, the particles 14 experience two different types of forces: acoustic radiation force ($F_{rad}$), and Stokes drag force ($F_{drag}$) [5]. Acoustic radiation force is caused by the scattering of sound waves on the particles, which moves the particles 14 either to a pressure node 32 or to an anti-node 34 depending on the physical properties of the particles 14. In particular, the radiation force is determined by the physical properties of particles and water. As known to a person skilled in the art, the relationship is given by the acoustic contrast factor, which is calculated based on the density and compressibility of particles and the fluid. When the acoustic contrast factor is positive, particles go to the pressure node; when it is negative, particles go to anti-node. In addition, the particle size determines the magnitude of the radiation force (although it does not change the direction of the force). A person skilled in the art would know how to use the standing wave to manipulate specific types of particles to the centre of the microfluidic channel. Stokes drag force is present due to the induced acoustic streaming flow, which has a direction opposite to that of the particle velocity relative to the flow stream. The motion of particles 14 inside the microfluidic channel 12 can be analysed by examining these two forces.

In use, the ultrasound transducer is configured to generate an acoustic force to cause the particles 14 to converge along a pre-defined path in the microfluidic channel 12. For example, the ultrasound transducer is adapted to produce an acoustic wave of a certain range of frequencies for a microfluidic channel with a given dimension such that the particles 14 are maintained at the centre path along the microfluidic channel 12 by acoustic forces as the fluid flows through the microfluidic channel 12.

Figure 3:
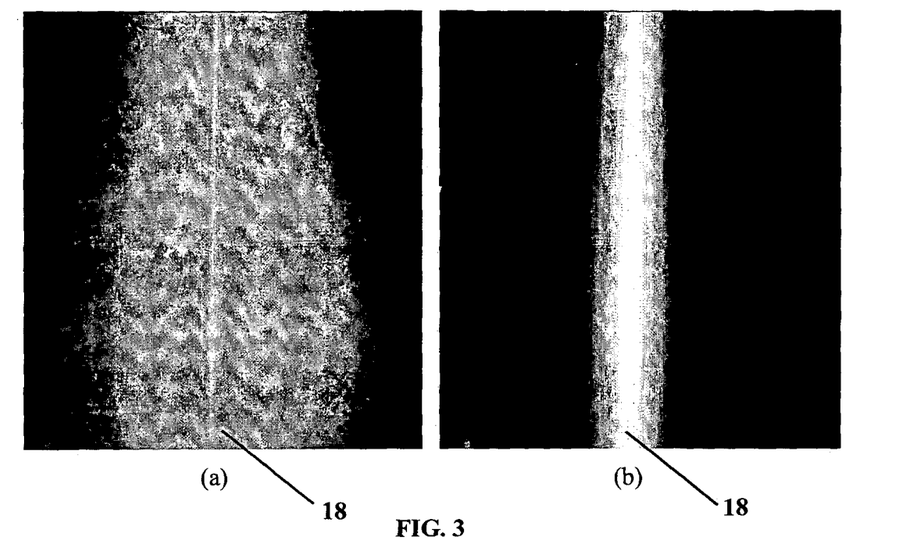

For example, in a microfluidic channel 12 with a height of 150 μm and a width of 400 μm, acoustic waves with 1.72 MHz and 7.12 MHz frequency are generated to respectively form acoustic resonance in the lateral and vertical direction along the microfluidic channel 12. In this example, the power of the acoustic transducer is in the range of 1 to 6 W. Since the acoustic force is proportional to the power, increasing the power accordingly increases the "focusing" efficiency. In general, higher power is preferred for samples with higher flow rate. However, the temperature of the fluid may increase with a higher power, which may result in the bubble formation in water that would disturb the detection. A person skilled in the art would know how to adjust the power of the acoustic transducer for specific applications or for use with a specific microfluidic device to achieve the intended purpose through routine experiments. The frequency of the acoustic wave is typically determined by the dimension of the channel such that its wavelength is about twice of a dimension (such as the width) of the channel. The pressure nodes formed by both standing waves coincide in the center 40 of the cross-section of the microfluidic channel 12 as shown in FIG. 2. FIGS. 3 (a) and (b) represent the profiles of particles distribution along the width of the microfluidic channel (top view) when the ultrasound transducers are switched off and on, respectively. As shown, when a sample suspension containing about 50 000 particles/μL of 5-μm polystyrene particles flows through the microfluidic channel with the flow rate of 0.1 mL/min, more than 90% of the particles are concentrated (focused) in a line (along the geometrical centre of the respective cross sections of the microfluidic channel) before they are discharged via the main outlet 18. The width of the line, which indicates the performance of the "focusing", can be adjusted by the electrical voltage applied to the acoustic transducer. In a particular example, the particles can be concentrated in an area with a width less than 10 μm (about 2.5% of the width 400 μm of the channel). Note that in FIG. 3(b), the line looks wider than its actual width due to the fluorescence brightness. Note that the term "concentrated" it not used here to imply that 100% of the particles are moved into the central line, but rather that the number of particles in that region is greater than would be the case statistically.

It will be appreciated by persons skilled in the art that various modifications can be made to the embodiments described above. For example, the device may have any number of ancillary outlets, or none and they do not need to be disposed symmetrically along the microfluidic channel. The ancillary outlets may be used for selectively discharging different types (also known as "sorting") of particles. The type and the number of acoustic transducers may vary. Typically, one or more ultrasonic transducers are used. The ultrasound transducers could be a piezoelectric transducer and magnetostrictive transducer. The typical ultrasonic frequency ranges from 20 to 200 kHz while the magnetostrictive transducer is typically limited to operate at frequencies below approximately 30 kHz. There are many types of ultrasound transducer that are generally labeled according to their design or intended usage. For example, contact transducers (e.g. a dual element, a linear array or a convex transducer) can be used by applying them directly to, or having contact with, a solid surface for analysis. Unlike contact transducers that are applied directly to solid surfaces, immersion transducers are submerged into liquids such as water and oil for analysis. The present inventors have found that flat contact piezoelectric transducers are particularly suitable in various embodiments.

For another example, in one embodiment, there is only a single ultrasonic transducer configured to generate two standing waves oscillating in directions orthogonal to each other. Typically, the two waves oscillate orthogonal to each other at the same frequency to produce two standing waves (i.e. in this case, the width and height of the channel are equal). Alternatively, at least two transducers are used to generate two standing waves oscillating in directions orthogonal to each other.

In yet another example, one or two standing waves are generated to oscillate in only one direction so as to converge the particles substantially into one plane (instead of one line) orthogonal to the cross-section of the channel. In the examples described above, the pressure node is provided along the microfluidic channel which coincides with the geometrical center of the respective cross sections of the microfluidic channel. In another embodiment, the pressure node formed by the standing wave offset from the geometrical center of the respective cross sections.

The acoustic transducers may be releasably attached to the structure defining the microfluidic channel or formed as an integral part of the structure defining the microfluidic channel. The acoustic transducers may be controlled by a control unit to generate waves at a different oscillating frequency or amplitude, upon the control unit receiving a control signal.

In a further embodiment, the fluid is another medium (such as beverage, blood, other biological fluid or biomedical samples) other than water. In one embodiment, the sensor detects microorganism particles in beverage for quality monitoring. In another embodiment, the sensor detects cells and/or bacteria in a blood sample (or other biological fluid or biomedical fluid samples) for biomedical analysis.

As shown in FIG. 1, the optofluidic sensor 10 further comprises an optical detection unit for detecting optical signals of the particles 14 as the particles flow through the microfluidic channel 12. The optical detection unit includes a laser source 24 for illuminating a fluid sample and a first sensor module 26 comprising one or more CMOS image sensors for detecting a first optical signal scattered by the sample. The optical detection unit further has a second sensor module 30 comprising a photo-detector unit made of one or more photodiodes for receiving a second optical signal scattered by the sample via an optical fiber 28. In practice, the microfluidic channel 12 is covered by a transparent top wall. For simplicity, this transparent top wall is omitted in FIG. 1.

The laser source 24 is positioned above the top wall of the channel to illuminate the sample in the microfluidic channel 12 from above. In use, the laser source 24 generates a coherent illumination (at a single wavelength or very narrow range of wavelengths) on the fluid sample with a sufficiently high intensity so as to produce such that the scattering signals are detectable by the sensor modules 26, 30. Typically, the power of the laser is in the range of 2-10 mW. As known to a skilled person in the art, if the power is low, the optical signal may not be strong enough to be detected whereas if the power is high, the noise level in the optical signal may be too high for effective signal processing. Typically, the wavelength of the laser is in the visible light range (400-650 nm) for producing a visible optical signal (such as images) directly. Other wavelengths may also be used as long as the particle is able to produce an effective scattering pattern and which is detectable by the sensor module(s). The exact wavelength may also be chosen based on the detector type (i.e. the wavelength with the highest sensitivity for the detector).

In a particular example, a compact optics is integrated with the laser source 24 to provide uniform and highly concentrated illumination onto a pre-defined detection area in the microfluidic channel 12. A first sensor module 26 is placed at the bottom wall of the microfluidic channel 12 to capture forward scattering patterns of the detected particles. In another embodiment, the optical fiber 28 is embedded in a side wall of the microfluidic channel 12 to collect side scattering signals to be detected by the photo-detector unit. In another embodiment, the forward scattering and side scattering signals are detected by an integrated optical detection unit or sensor module.

Figure 4:
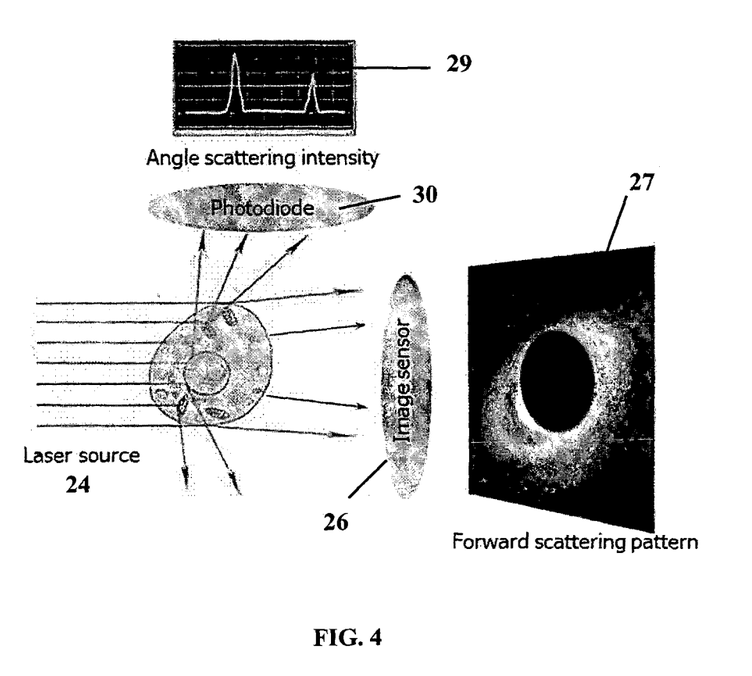
FIG. 4 is a schematic illustration of an optical detection unit for measuring optical scattering signals of microorganism particles.

Scattering signals (e.g. the pattern and intensity) may be affected by relative location, such the distance, between the particles and the sensor modules and/or the light source, and even different detection locations along channel. In order to achieve the most consistent detection of particles and minimize random errors, the microorganism particles may be concentrated and aligned in a microfluidic channel by acoustic forces using the techniques described in earlier examples. In particular, the particles are arranged to pass through the channel along a predetermined path sequentially thereby allowing the scattering signals to be detected at a localized detection area (as the laser spot size (e.g. with a diameter of 20 μm) is typically very small compared to the channel dimensions (e.g. 300 μm)) with the same optical detection system. Typically, the laser spot size is smaller than the channel size to avoid boundary diffraction caused by the channel walls. As a particle of the sample flows through the detection area of the microfluidic channel, it scatters the light in all directions (see FIG. 4) thereby modifying an optical signal 27, 29 as the light intensity received by the first and/or the second sensor modules 26, 30. This enables the detection of the presence of particles in a fluid sample.

Furthermore, the present inventors have discovered that the scattering signals of a particle, and especially a microorganism particle, is correlated with its morphologies (e.g. size, shape) and biophysical properties (e.g. refractive index). Therefore, this additionally allows the characterization of particles based on their scattering signals. In one embodiment, this allows the identification of the specific type of the microorganism particles.

Figure 5:
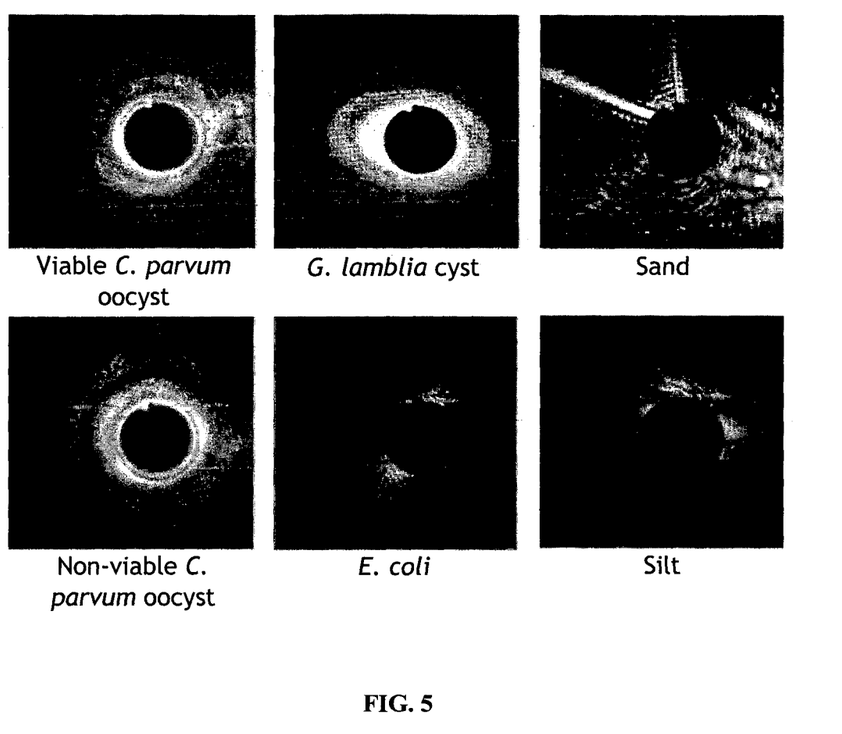
FIG. 5 shows forward scattering patterns of some of possible particles in water, including viable and non-viable C. parvum oocyst, G. lamblia cyst, Escherichia coli (E. coli), sand and silt.

For example, it is noted that forward scattering patterns of particles are related to their biophysical properties, such as the size, shape and internal composition structures. Thus, different microorganism particles have distinctive forward scattering patterns. FIG. 5 illustrates typical forward scattering patterns exhibited by different types of particles in water, including *C. parvum* oocyst, *G. lamblia* cyst, *E. coli*, sand and silt.

Figure 6:
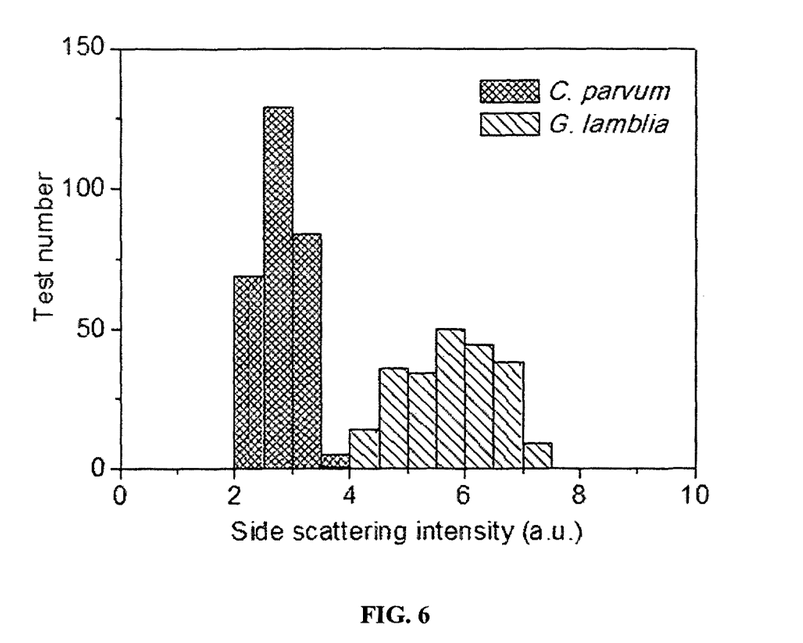
FIG. 6 shows side scattering intensity measurements of C. parvum oocyst and G. lamblia cyst.
Figure 7:
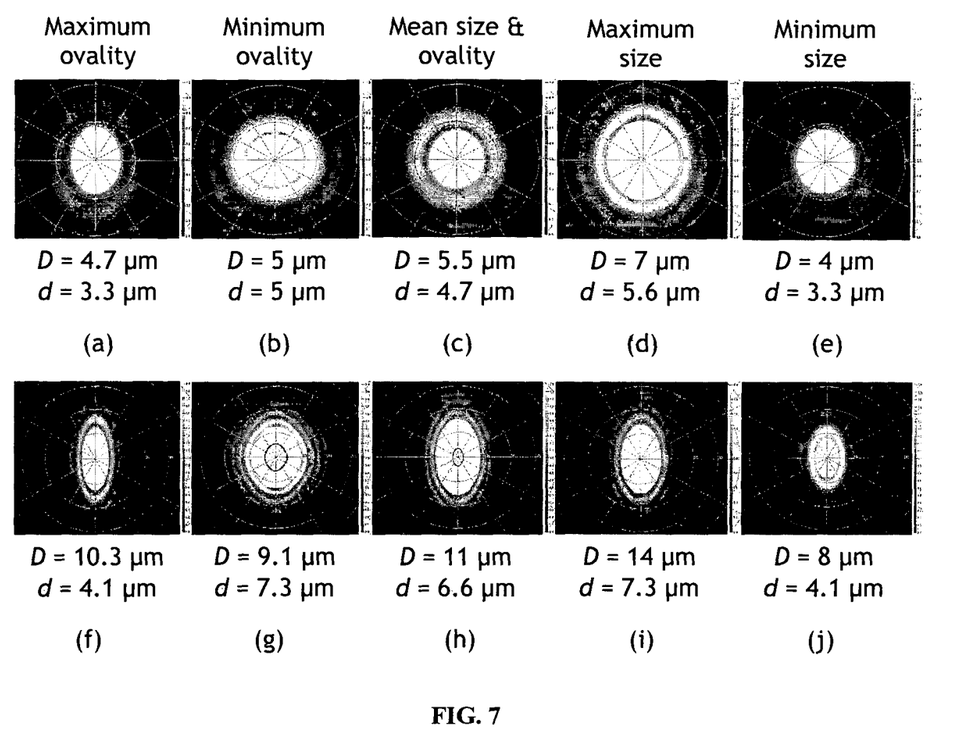
FIG. 7 shows simulation of forward scattering patterns of (a)-(e) C. parvum oocyst and (e)-(j) G. lamblia cyst with different sizes and ovalities (D and d are the major and minor diameters of the microorganism particle, respectively).

Similarly, particles with different size, shape, refractive index and granular structure have distinct side scattering signals such as side scattering intensities. Generally, the peak amplitude is determined predominantly by the particle size. For example, particles of a larger size tend to have a higher side scattering intensity and longer transition duration when flow through the channel (and the pre-defined detection area). For example, the intensity of side scattering signal of a *G. lamblia* cyst with the size ranging from 8 to 12 μm is much higher than that of a *C. parvum* oocyst with the size ranging from 4 to 6 μm, as shown in FIG. 6.

In one embodiment, the types of microorganism particles in the sample are characterized or identified based on the forward scattering patterns of the particles In another embodiment, the characterization or identification is made based on a combination of the forward scattering and side scattering signals, as detected by the respective sensor modules when the particles flow through the microfluidic channel. In this case, the side scattering signal provides additional information, which may not be exhibited in the forward scattering pattern and this helps to increase the recognition accuracy.

In one embodiment, the side scattering signal may be transformed into a transistor-transistor logic (TTL) signal through a comparator that is connected with the trigger pins of the first sensor module 26. Upon the triggering pins being activated, the first sensor module 26 is initiated to capture the forward scattering patterns. In this way, continuous monitoring of the optical signals by the first sensor module 26 is not required and this will improve data handling and processing efficiency thereby reducing computational load.

In one embodiment, the optofluidic sensor 10 is provided with a data processor (such as a computer process) for processing the optical signals collected by the sensor modules 26, 30. For example, the computer processor is configured to receive the optical signals from the sensor modules (e.g. the forward scattering patterns and/or the side scattering signal) and characterize microorganism particles based on a comparison against a plurality of reference signals in a database representing typical signal profiles of known particles. In one embodiment, this enables the identification of a specific species of the microorganism particles.

In one example, the computer processor employs a classifier to characterize the microorganism particle. The classifier can be trained using supervised learning to identify the type of the particle. In particular, machine learning can be employed to train the classifier using a database comprising scattering signatures of known particles. The database contains both forward and side scattering signatures (i.e. typical signal profiles) exhibited by a range of microorganism particles that may exist in water. The classifier is trained to analyze an input optical signal associated with the detected particle and assign particles into a class representing a group of particles with a certain characteristics or a specific species of microorganism particles. For example, algorithms such as principal component analysis (PCA), support vector machine (SVM) and/or neutral network may be used to obtain the classifier to extract and recognize the features from the optical signal. In the process, the following features of scattering patterns can be employed as parameters for training the algorithm (i.e. the classifier) image quality and statistical evaluation, radiometric correction, geometric correction, image enhancement and sharpening, phase correlation, rotational and scale parameter, etc. In a particular example, 400 scattering patterns with different parameters such as size, ovality and refractive index for the same species are obtained and their signature features are extracted.

In one example, some forward scattering patterns of C. parvum oocyst (see FIG. 7(a)-FIG. 7(e)) and G. lamblia cyst (see FIG. 7(f)-FIG. 7(j)) are obtained by simulation. In this particular example, the simulation is carried out by finite-difference time-domain (FDTD) method using Mie scattering theory. These scattering patterns are simulated with by varying a plurality of parameters such as particle size, ovality and refractive index while the value of parameter is varied based on measured value of the parameter of known particles. For example, the particles with mean, maximum and minimum size are simulated. For certain species, the refractive index variation is very small (<0.001), so all the scattering patterns may be simulated with the mean refractive index for the same species. The size and ovality are usually distributed in a wide range. For a certain ovality, a group of patterns are simulated in the detected size range with minor variations. Similarly, a group of simulating patterns can be obtained with a fixed size and minor variations in ovality. Typically, 400 simulating scattering patterns/images with different parameters will be generated for the same species.

As explained earlier, the database comprises scattering signatures for known microorganism particles or pathogens in water. In one example, for each type microorganism particle (or microorganism species), there are a plurality of scattering signatures corresponding to the type of microorganism particle. These scattering signatures represent morphological features typically present in forward scattering patterns of known particles. The scattering signatures may be a plurality of images corresponding to typical scattering patterns or images of a particular type or species of microorganism particles. The scattering signature has information associated with, such as being an image of, the forward scattering patterns of the particles. Preferably, the database has no more than 400 images for each type of microorganism to so as to effective encompass key information (e.g. typical variations in the morphological features) associated with the identity of the particle while maintaining the database at a relatively small size (e.g. with a minimal number of images).

The scattering signatures may be derived from the simulated scattering patterns as described above. For example, in obtaining the simulated patterns, several parameters (i.e. size, ovality, refractive index) may be varied in the simulation to produce generally different patterns. In some cases, a different combination of the parameters may result in the same or very similar scattering patterns. In choosing the scattering signatures, the duplicated scattering patterns may be removed to reduce the database size. In a further example, the simulated scattering patterns are compared with measured scattering patterns of known particles so as to evaluate which of the simulated scattering patterns are better representations of the scattering signatures, and only those simulated scattering patterns are chosen to be the scattering signatures.

According to a particular example, the database contains FIG. 7(a)-FIG. 7(e) and FIG. 7(f)-FIG. 7(j) as a part of the scattering signatures of C. parvum oocyst and G. lamblia cyst, respectively.

In another example, the scattering signatures are derived from measured (rather than simulated) scattering patterns of known microorganism particles.

In use, the one or more sensor modules capture the scattering signals from each of particles and the data processing module employs a classifier to compare the captured signals with the scattering signatures corresponding to various types of microorganism particle in the database and to identify the particle species based on the comparison.

Figure 8:
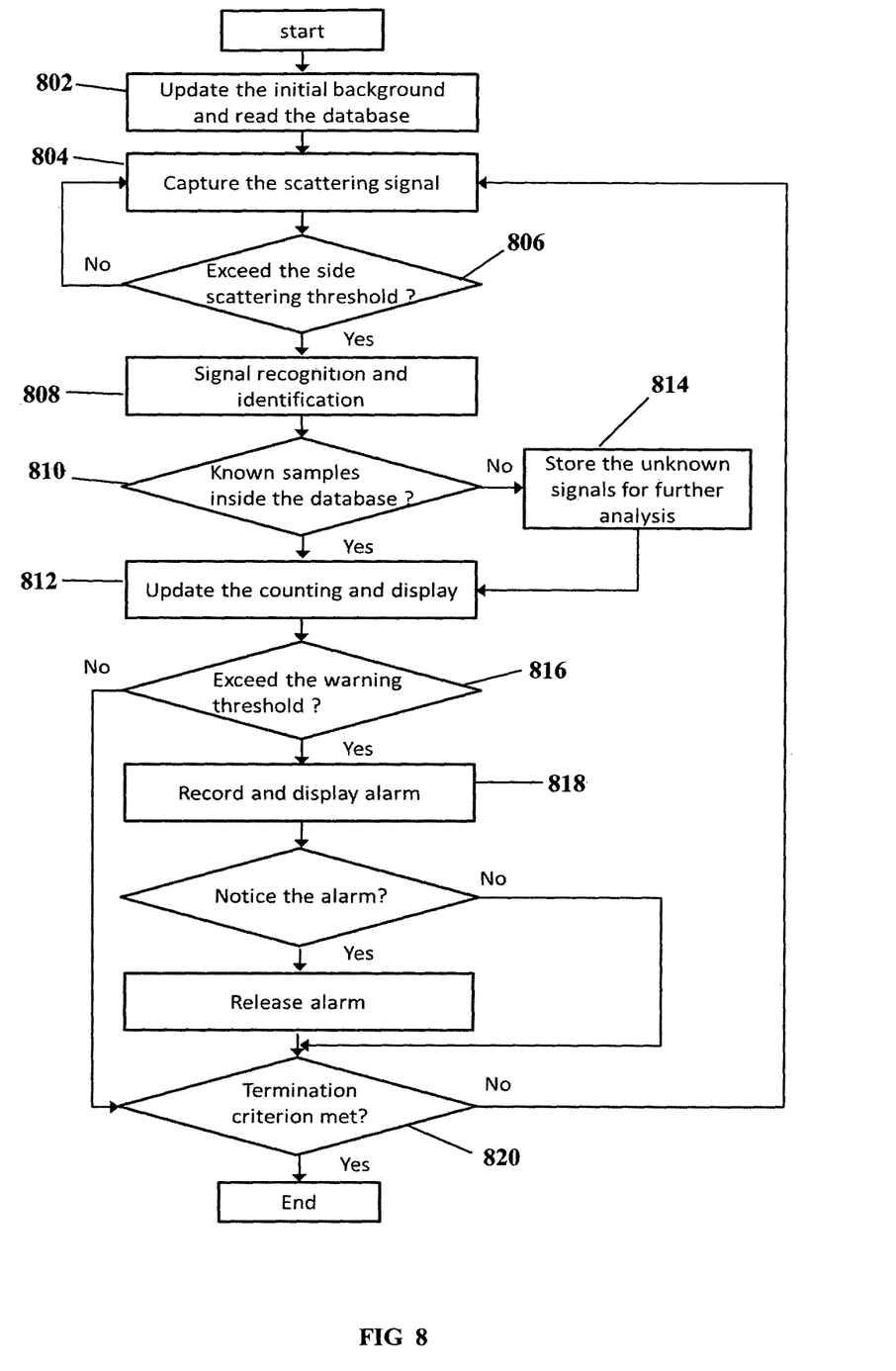
FIG. 8 is a flow chart illustrating an embodiment of the water risk management system employing the sensor.

FIG. 8 is a flow chart illustrating an embodiment of a real-time water risk management system. The system detects and identifies particles in a water sample and produces a warning signal if the particles in the water are determined to be above a certain risk level. Before the detection, an integrated scattering signal database is made accessible by a data processing module of the system and the warning levels for all the species in the database are set independently. The integrated scattering signal database contains at least forward scattering signatures (and optionally side scattering signatures) of known microorganisms for comparing against detected optical signals from particles in the water sample. The forward scattering signatures represent typical forward scattering patterns.

At step 802, an initial background signal is captured once the system is activated, which will be updated at predetermined intervals. When a side scattering signal is detected at step 804, it triggers the first sensor module to capture an image simultaneously. The effective forward scattering pattern is obtained by subtracting the background signal from the captured image. In one example, the forward scattering pattern is combined with the side scattering signal to form a combined scattering signature.

A side scattering threshold is optionally provided to allow the initiation of signal recognition and identification 808 once the received signals above the threshold. In one example, the threshold is set based on the typical side scattering signal of known waterborne microorganism particles. Signal recognition and identification 808 is performed to classify the particles into a particle category or a specific species based on the database at step 810 and the particle count (for a specific category or total) is updated 812 by the system. If the particle is classified into an "unknown category" by the classifier, the signal may be stored and subject to further processing 814. For example, the unknown particle can be identified by other detection methods such as by an electron microscopy. Once the particle has been identified, the signal will be added into the database to be associated with the corresponding particle species. If the particle belongs to a new species, a new category may be created in the database.

A test is carried out at 816 to determine whether the count is above a warning threshold (there may be a warning threshold for each specific category and/or one for the total number of particles). If it is determined that the particle count for a certain category of particle exceeds a pre-defined value, a warning signal, for example, an alarm will be triggered 818. Optionally, a water treatment plan can be devised based on the pathogen level and category to treat the water from which the water sample is taken. If it is determined that the particles in the water do not exceed the warning threshold, the system will continue to capture the scattering signals 804 unless a termination criterion is met 820. For example, the process is terminated if the particle count for a certain, category of particle exceeds a predefined value. In another example, the termination criterion is met when all the fluid sample has been tested.

The above process can be carried out by a processor (which may be referred to as a central processor unit or CPU) and a data storage device which stores instructions operative by the processor to cause the processor to perform the process above. The processor may be implemented as one or more CPU chips. The data storage device may be implemented as a floppy disk, optical disc, hard disk drive, flash memory card, or any other types of recording medium.

Figure 9:
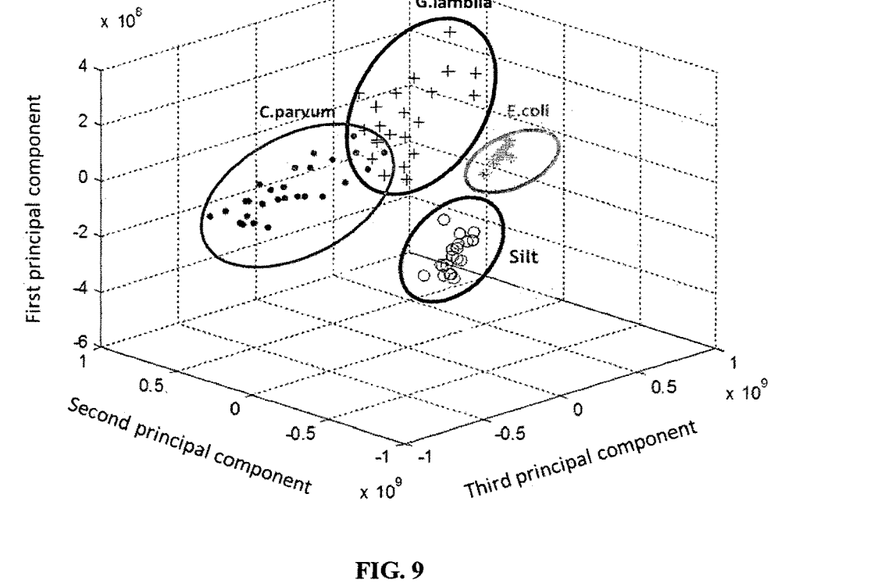
FIG. 9 is the scattering signature classification of C. parvum oocyst, G. lamblia cyst, E. coli sand and silt.

An approach to verify the possibilities of using the optical scattering signals for pathogens detection in water is to build up a database of the optical scattering signals based on different pathogen species. FIG. 9 shows different clusters (corresponding to different scattering signature classifications) obtained by the PCA for C. parvum oocyst, G. lamblia cyst, E. coli and silt. In this example, the scattering signals which include greyscale images of forward scattering patterns from known particles are obtained, for example, by directly capturing their forward scattering patterns using a camera. The greyscale image is then converted into a matrix and PCA is employed for further analysis. PCA is a statistical procedure that uses an orthogonal transformation to convert a set of observations of possibly correlated variables into a set of values of linearly uncorrelated variables called principal components. The first principle component typically represents the linear combination of the variables that has maximum variance (among all linear combinations). Thus, this accounts for as much variation in the data as possible. The second principal component represents the linear combination of variables that accounts for as much of the remaining variations as possible, with the constraint that the correlation between the first and second components is 0. Further principle components (such as the $i^{th}$ principle component) may be added in a similar way. Generally, the number of principal components is less than or equal to the number of original variables. In this particular example, the first three principle components are chosen to represent the typical features of the scattering patterns.

It can be seen that the scattering signatures of C. parvum oocyst and G. lamblia cyst can be effectively discriminated from those of E. coli and silt. Some scattering signatures of C. parvum oocyst are assigned to the cluster containing G. lamblia cyst, primarily because there are overlapping between physical properties of these two species. For scattering signatures of C. parvum oocyst, 77% of them are correctly classified as C. parvum oocyst and 13% of them are classified as G. lamblia cyst, while the rest are identified as unknown. For scattering signatures of G. lamblia cyst, 88% of them are classified as G. lamblia cyst and 9% of them are classified as C. parvum oocyst, while the rest are identified as unknown. Due to distinct physical properties and the resulting scattering signatures, E. coli and silt can be clearly differentiated from other species.

Figure 10:
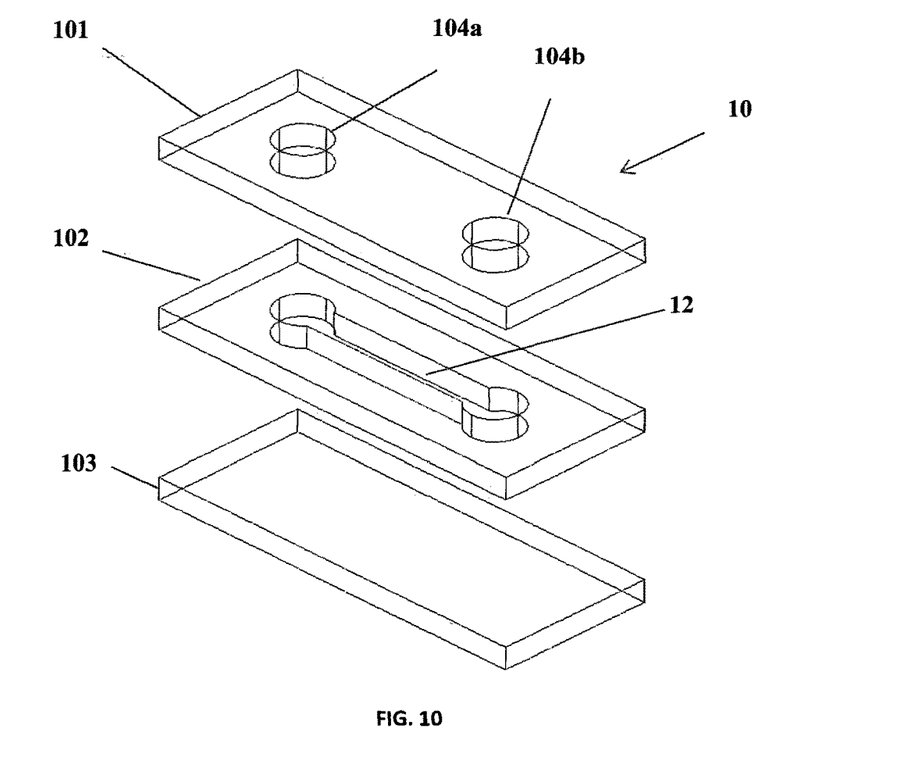
FIG. 10 shows schematically the construction of a sensor in a variant of the embodiment of FIG. 1.

According to a particular example, the sensor 10 can be formed by joining three layers of substrates (top, middle and bottom layers) together. This is illustrated in FIG. 10, in which the three layers are shown as 101, 102 and 103. This is a variant of the embodiment of FIG. 1 in that the ancillary outlets 20a, 20b are omitted. The top layer 101 and the bottom layer 103 are transparent, hard substrates, such as Pyrex 7740 glass wafers. The middle layer 102 is a hard substrate such as a silicon or glass wafer, and may be for example be of 300 µm thickness. Prior to joining, the microfluidic channel 12 of the optofluidic sensors is formed in the middle layer 102 by patterning by photolithography. For example, the wafer is etched through (thereby forming the channel without the bottom wall) to form a microstructured wafer. The etching can be performed using deep RIE machine for a suitable period of time known to a skilled person in the art, for example, the etching time is 60 mins for a silicon wafer of 300 µm thickness. Two holes 104a, 104b are drilled through the top layer 101, to form an inlet and outlet of the microfluidic channel. It will be appreciated by a skilled person that the holes can be patterned by other techniques such as etching. Then the micro-structured wafer (the middle layer 102) is sandwiched between the drilled wafer (the top layer 101) and the bottom layer 103, and the three layers 101, 102 103 are bonded by a thermal bonding technique or by glue. Top layer 101 forms the transparent top wall of the microfluidic channel 12, and part of the upper surface of the bottom layer 103 provides the floor of the microfluidic channel 12.

Alternatively, the sensor may be formed at an integral part by selectively etching a single piece of substrate.

The dimension of the microfluidic device—the "chip" (for example, 6 cm by 1 cm) can be standardized by using a wafer dicing machine. The typical dimension of the microfluidic channel is about 1~10 cm in length, 80~600 µm µm in width, and 200~400 µm in height. In a specific example, the dimension of the entire sensor device (with the detectors and signal processing unit) is about 100 mm×100 mm×150 mm (height×width×length).

An optofluidic sensor as described above has been fabricated and experimentally investigated for real-time waterborne pathogenic microorganisms monitoring and detection which did not require fluorescent-labeling. The forward scattering patterns and side scattering signal of possible microorganisms are collected using the optofluidic system. In combination with pattern recognition methods, the protozoan parasites can be identified effectively. The results demonstrate that a mean recovery rate of 65% for C. parvum oocyst and 72% for G. lamblia cyst can be achieved, respectively. The present inventors have found that the sensor works well with particles with a size equal to or larger than 0.5 µm, and especially particle sizes between 0.5 µm to 20 µm. The larger the particles are, the easier for the sensor to correctly characterize or identify the particles. When the particle size is smaller than 0.5 µm, there appears to be some difficulties with the acoustic "focusing" of the particles.

It will be appreciated by persons skilled in the art that various modifications can be made to the embodiments described above. For example, other types of optical sensors other thane CMOS sensors and photodiodes can be used for detecting optical signals from the particles. The particles to be detected are not limited to microorganism particles but also other particles like sand particles. A skilled person would also appreciate that the sensor modules can be arranged at a different location with respect to the fluidic channel. For example, the laser source can be arranged to illuminate the particles from the side. In this case, a sensor module may be provided at the opposite side to capture forward scattering patterns.

In one embodiment, the particles are concentrated onto the center line (i.e. a center path along which the fluidic flows in the fluidic channel) of the microfluidic channel. In another embodiment, the particles are concentrated onto a path that is offset from the center line of the microfluidic channel. In yet another embodiment, the particles are substantially converged on one plane instead of a line or path along the channel.

In one embodiment, no trigger is required for activating the first sensor module 26. Rather, the first sensor module continuously monitors the optical signals in real time to capture a plurality of images of forward scattering patterns of the particle. It is also understood by a skilled person that the forward and scattering optical signals could be pre-processed to remove noises or other artifacts before the features are extracted for characterization or classification of the particle.

Similarly, the characterization of a particle involves associating a range of physical properties (such as particle size, refractive index or other morphological features) with the particle, and it does not require identifying particles as specific species. Identification of particles may also encompass a determination as to the viability of particles of the particular species.

The inventions illustratively described herein may suitably be practiced in the absence of any element or elements, limitation or limitations, not specifically disclosed herein. Thus, for example, the terms "comprising, including", "containing", etc. shall be read expansively and without limitation, Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

REFERENCES

The following references are hereby incorporated by reference in their entirety and for all purposes:
[1] M. M. Marshall, D. Naumovits, Y. Ortega and C. R. Sterling, "Waterborne protozoan pathogens", Clin. Microbiol. Rev. 10, 67-85(1997).
[2] J. P. Robinson, B. P. Rajwa, M. M. Dundar, E. Bae, V. Patsekin, E. D. Hirleman, A. Roumani, A. K. Bhunia, J. E. Dietz, V. J. Davisson and J. G. Thomas, "A distributed national network for label-free rapid identification of emerging pathogens," Proc. SPIE 8018, Chemical, Biological, Radiological, Nuclear, and Explosives (CBRNE) Sensing XII, 80180C, 3 Jun. (2011).
[3] C. L. DiGiorgio, D. A. Gonzalez, and C. C. Huitt, "*Cryptosporidium* and *Giardia* recoveries in natural waters by using environmental protection agency method 1623," Appl. Environ. Microbiol. 68, 5952-5955(2002).
[4] United States Environmental Protection Agency, EPA 815-R-05-002, "Method 1623:*Cryptosporidium* and *Giardia* in water by filtration/IMS/FA," December 2005.
[5] L. P. Gorkov, "On the forces acting on a small particle in an acoustical field in an ideal fluid," Sov. Phys. Dokl. 6, 773-(1962).

The invention claimed is:

1. A method of managing water risk comprising:
(a) receiving optical signals scattered by a microorganism particle in the fluid, said optical signals comprising a forward scattering pattern;
(b) characterizing the microorganism particle into one of a plurality of categories based on the forward scattering pattern using a classifier that employs a machine learning algorithm;
(c) updating a record data representing the number of microorganism particles of the plurality of categories;
(d) determining a risk level based on the record data;
(e) comparing the risk level to a reference level; and
(f) depending on the result of the comparison, producing a warning signal indicating an elevated risk of pathogens in the fluid,
wherein the machine learning algorithm extracts features of the detected optical signals of the particles, assigns the respective particles into respective categories based on the features, and forms a database based on the features,
wherein the machine learning algorithm includes at least one parameter chosen from: image quality, statistical evaluation, radiometric correction, geometric correction, image enhancement and sharpening, phase correlation, and rotational and scale parameter, and
wherein the database includes both forward scattering signatures and side scattering signatures.

2. A fluid risk management system comprising a computer processor and a data storage device, the data storage device storing instructions operative by the processor to cause the processor to perform the method of claim 1.

* * * * *